US012564333B2

(12) United States Patent
Tsuji

(10) Patent No.: US 12,564,333 B2
(45) Date of Patent: Mar. 3, 2026

(54) SETTING DEVICE, SETTING METHOD, AND SETTING PROGRAM

(71) Applicant: FUJIFILM CORPORATION, Tokyo (JP)

(72) Inventor: Tetsuya Tsuji, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 327 days.

(21) Appl. No.: 18/188,462

(22) Filed: Mar. 23, 2023

(65) Prior Publication Data

US 2023/0225632 A1     Jul. 20, 2023

Related U.S. Application Data

(63) Continuation of application No. PCT/JP2021/028494, filed on Jul. 30, 2021.

(30) Foreign Application Priority Data

Sep. 25, 2020     (JP) ................................. 2020-161414

(51) Int. Cl.
| | | |
|---|---|---|
| *A61B 5/107* | (2006.01) | |
| *A61B 8/00* | (2006.01) | |
| *G16H 30/40* | (2018.01) | |

(52) U.S. Cl.
CPC .......... *A61B 5/1075* (2013.01); *A61B 8/5223* (2013.01); *G16H 30/40* (2018.01)

(58) Field of Classification Search
CPC ... A61B 5/0077; A61B 5/1075; A61B 5/1079; A61B 5/4869; A61B 5/4872;

(Continued)

(56) References Cited

U.S. PATENT DOCUMENTS

| | | | | |
|---|---|---|---|---|
| 4,160,906 A | * | 7/1979 | Daniels ................ | G05B 19/106 378/118 |
| 2004/0141582 A1 | * | 7/2004 | Ono ........................ | A61B 6/544 378/42 |

(Continued)

FOREIGN PATENT DOCUMENTS

| | | |
|---|---|---|
| EP | 0346530 A1 | 12/1989 |
| JP | 2000-012280 A | 1/2000 |

(Continued)

OTHER PUBLICATIONS

International Search Report issued in International Application No. PCT/JP2021/028494 on Oct. 5, 2021.

(Continued)

*Primary Examiner* — David J Makiya
*Assistant Examiner* — Soorena Kefayati
(74) *Attorney, Agent, or Firm* — SOLARIS Intellectual Property Group, PLLC

(57)     ABSTRACT

A setting device comprising at least one processor, wherein the processor is configured to: acquire imaging part information indicating an imaging part of a subject whose radiographic image is captured by radiation emitted from a radiation emitting device; acquire body thickness information indicating a body thickness of the subject in a direction in which the radiation is transmitted; acquire condition information indicating whether a tube voltage value and a mAs value are each set to variable or fixed; and derive a set value of the tube voltage and a set value of the mAs value of the radiation emitting device for emitting the radiation such that a dose of the radiation transmitted through the imaging part is the same as a dose at a reference body thickness, on the basis of the imaging part information, the body thickness information, and the condition information.

11 Claims, 6 Drawing Sheets

(58) Field of Classification Search
CPC ... A61B 5/7264; A61B 8/5223; A61B 5/7292; A61B 6/542; A61B 6/488; A61B 6/544; A61B 6/5217; A61B 6/545; A61B 6/588; A61B 6/589; G16H 30/20; G16H 30/40; G16H 40/63; G16H 50/20; G16H 50/30

See application file for complete search history.

(56) References Cited

U.S. PATENT DOCUMENTS

| | | | | |
|---|---|---|---|---|
| 2015/0093013 | A1* | 4/2015 | Morita | A61B 6/5205 |
| | | | | 382/132 |
| 2015/0100290 | A1* | 4/2015 | Falt | G16H 50/50 |
| | | | | 703/2 |
| 2016/0089104 | A1* | 3/2016 | Naito | A61B 6/4417 |
| | | | | 600/449 |
| 2017/0055933 | A1* | 3/2017 | Kawamura | G06T 11/005 |
| 2018/0116622 | A1* | 5/2018 | Jan | A61B 6/405 |
| 2018/0199907 | A1* | 7/2018 | Hatakeyama | H05G 1/26 |
| 2018/0220979 | A1* | 8/2018 | Kojima | A61B 6/542 |
| 2018/0299565 | A1* | 10/2018 | Cresens | G01T 1/1645 |
| 2019/0059829 | A1* | 2/2019 | Han | A61B 6/469 |

FOREIGN PATENT DOCUMENTS

| | | |
|---|---|---|
| JP | 2010-102877 A | 5/2010 |
| JP | 2016-106953 A | 6/2016 |
| JP | 2018-082997 A | 5/2018 |

OTHER PUBLICATIONS

Written Opinion of the ISA issued in International Application No. PCT/JP2021/028494 on Oct. 5, 2021.

Extended European Search Report dated Feb. 12, 2024, issued in corresponding EP Patent Application No. 1 21871978.9.

Office Action dated Dec. 16, 2024, issued by the EPO in corresponding EP Patent Application No. 21871978.9.

Office Action dated May 14, 2025, issued by the EPO in corresponding EP Patent Application No. 21871978.9.

* cited by examiner

FIG. 5
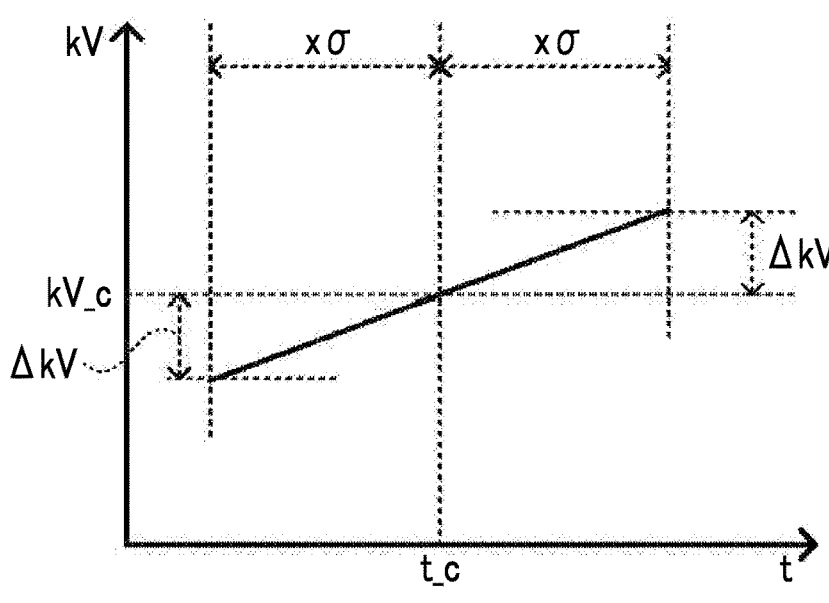
FIG. 6
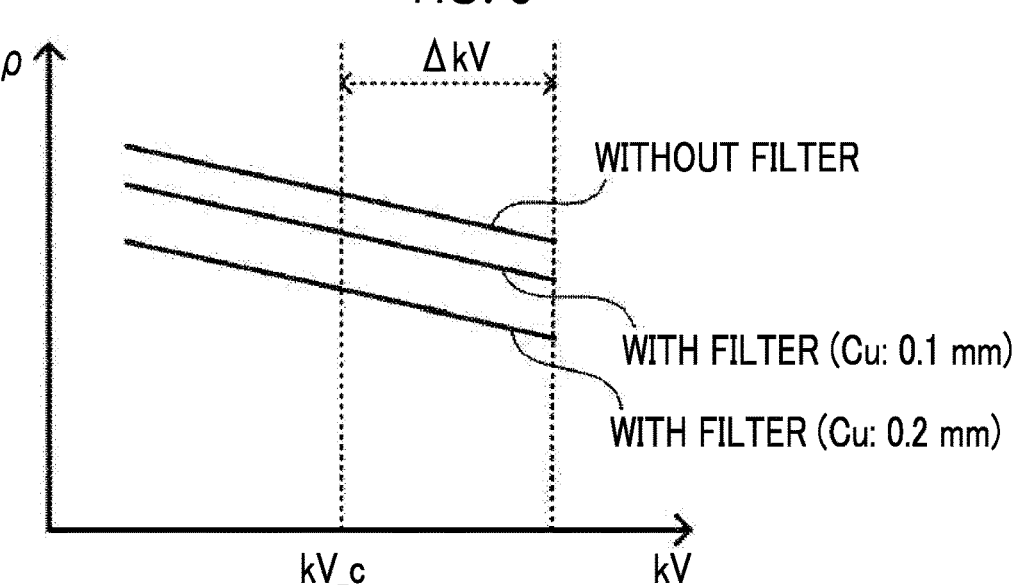
FIG. 7
| TYPE | DOSE RATIO B |
|------|--------------|
| CR | 1.7 |
| GOS | 1.0 |
| CsI | 0.6 |
~70

SETTING DEVICE, SETTING METHOD, AND SETTING PROGRAM

CROSS REFERENCE TO RELATED APPLICATIONS

This application is a continuation of International Application No. PCT/JP2021/028494, filed on Jul. 30, 2021, which claims priority from Japanese Patent Application No. 2020-161414, filed on Sep. 25, 2020. The entire disclosure of each of the above applications is incorporated herein by reference.

BACKGROUND

Technical Field

The present disclosure relates to a setting device, a setting method, and a setting program.

Related Art

In general, in a case in which a radiographic image of a subject is captured by radiation emitted from a radiation emitting device, imaging conditions related to a tube voltage and a mAs value of a radiation source that emits the radiation are set for the radiation emitting device. For example, JP2010-102877A discloses a technique that sets either an imaging time priority mode in which an increase in a tube voltage is allowed rather than an extension of an imaging time as imaging conditions or a tube voltage priority mode in which the extension of the imaging time is allowed rather than the increase in the tube voltage.

However, it is desired to set a tube voltage and a mAs value according to an imaging part and a body thickness of a subject. In some cases, the technique disclosed in JP2010-102877A is not sufficient to set the tube voltage and the mAs value according to the imaging part and the body thickness of the subject for each imaging condition set in the radiation emitting device.

SUMMARY

The present disclosure has been made in view of the above circumstances and provides a setting device, a setting method, and a setting program that can easily set a tube voltage and a mAs value corresponding to an imaging part and a body thickness of a subject for each imaging condition set in a radiation emitting device.

According to a first aspect of the present disclosure, there is provided a setting device comprising at least one processor. The processor acquires imaging part information indicating an imaging part of a subject whose radiographic image is captured by radiation emitted from a radiation emitting device, acquires body thickness information indicating a body thickness of the subject in a direction in which the radiation is transmitted, acquires condition information indicating whether an imaging condition set in the radiation emitting device is a first condition in which a tube voltage value is a fixed value and a mAs value is a variable value, a second condition in which the tube voltage value is a variable value and the mAs value is a fixed value, or a third condition in which the tube voltage value is a variable value and the mAs value is a variable value, and derives a set value of the tube voltage and a set value of the mAs value of the radiation emitting device for emitting the radiation such that a dose of the radiation transmitted through the imaging part is the same as a dose at a reference body thickness, on the basis of the imaging part indicated by the imaging part information, the body thickness indicated by the body thickness information, and the condition indicated by the condition information.

According to a second aspect of the present disclosure, in the setting device according to the first aspect, the processor may derive the set values using at least one of an SID, the imaging part, a filter added to a radiation source, a type of a radiation detector that detects the radiation, adjustment information related to adjustment of the tube voltage with respect to the body thickness, or a concentration in AEC.

According to a third aspect of the present disclosure, in the setting device according to the second aspect, the reference body thickness may be determined on the basis of at least one of the imaging part, a race, a gender, an age, or a ratio of muscle to fat in the subject, and the processor may use a reference tube voltage corresponding to the reference body thickness as the adjustment information.

According to a fourth aspect of the present disclosure, in the setting device according to the first aspect or the second aspect, in a case in which the condition indicated by the condition information is the first condition and the third condition, the processor may derive the set value of the mAs value corresponding to the body thickness indicated by the body thickness information, using a linear attenuation coefficient for the tube voltage.

According to a fifth aspect of the present disclosure, in the setting device according to any one of the first to fourth aspects, in a case in which the condition indicated by the condition information is the second condition, the processor may derive the set value of the tube voltage on the basis of at least one of the imaging part indicated by the imaging part information, a reference tube voltage corresponding to the reference body thickness, or a filter added to a radiation source and the body thickness indicated by the body thickness information.

According to a sixth aspect of the present disclosure, in the setting device according to any one of the first to fifth aspects, the processor may acquire the imaging part information from an imaging menu.

According to a seventh aspect of the present disclosure, in the setting device according to any one of the first to sixth aspects, the processor may acquire the body thickness information by subtracting an SSD from an STD to derive the body thickness.

According to an eighth aspect of the present disclosure, in the setting device according to any one of the first to sixth aspects, the processor may acquire the body thickness information by subtracting an SSD and a TID from an SID to derive the body thickness.

According to a ninth aspect of the present disclosure, in the setting device according to any one of the first to eighth aspects, the processor may output the set value of the tube voltage and the set value of the mAs value to the radiation emitting device.

In addition, according to a tenth aspect of the present disclosure, there is provided a setting method executed by a processor. The setting method comprises: acquiring imaging part information indicating an imaging part of a subject whose radiographic image is captured by radiation emitted from a radiation emitting device; acquiring body thickness information indicating a body thickness of the subject in a direction in which the radiation is transmitted; acquiring condition information indicating whether an imaging condition set in the radiation emitting device is a first condition in which a tube voltage value is a fixed value and a mAs value is a variable value, a second condition in which the tube voltage value is a variable value and the mAs value is a fixed value, or a third condition in which the tube voltage value is a variable value and the mAs value is a variable value; and deriving a set value of the tube voltage and a set value of the mAs value of the radiation emitting device for emitting the radiation such that a dose of the radiation transmitted through the imaging part is the same as a dose at a reference body thickness, on the basis of the imaging part indicated by the imaging part information, the body thickness indicated by the body thickness information, and the condition indicated by the condition information.

Further, according to an eleventh aspect of the present disclosure, there is provided a setting program that causes a processor to execute a process comprising: acquiring imaging part information indicating an imaging part of a subject whose radiographic image is captured by radiation emitted from a radiation emitting device; acquiring body thickness information indicating a body thickness of the subject in a direction in which the radiation is transmitted; acquiring condition information indicating whether an imaging condition set in the radiation emitting device is a first condition in which a tube voltage value is a fixed value and a mAs value is a variable value, a second condition in which the tube voltage value is a variable value and the mAs value is a fixed value, or a third condition in which the tube voltage value is a variable value and the mAs value is a variable value; and deriving a set value of the tube voltage and a set value of the mAs value of the radiation emitting device for emitting the radiation such that a dose of the radiation transmitted through the imaging part is the same as a dose at a reference body thickness, on the basis of the imaging part indicated by the imaging part information, the body thickness indicated by the body thickness information, and the condition indicated by the condition information.

According to the present disclosure, it is possible to easily set the tube voltage and the mAs value corresponding to the imaging part and body thickness of the subject for each imaging condition set in the radiation emitting device.

BRIEF DESCRIPTION OF THE DRAWINGS

FIG. 5 is an example of a graph illustrating a correspondence relationship between a body thickness of a subject and a set value of a tube voltage.

FIG. 6 is an example of a graph illustrating a correspondence relationship between the set value of the tube voltage and a linear attenuation coefficient.

FIG. 7 is a diagram illustrating an example of correspondence relationship information indicating a correspondence relationship between the type of radiation detector and a dose ratio.

DETAILED DESCRIPTION

Hereinafter, embodiments of the invention will be described in detail with reference to the drawings. In addition, each of the embodiments does not limit the invention.

Figure 1:
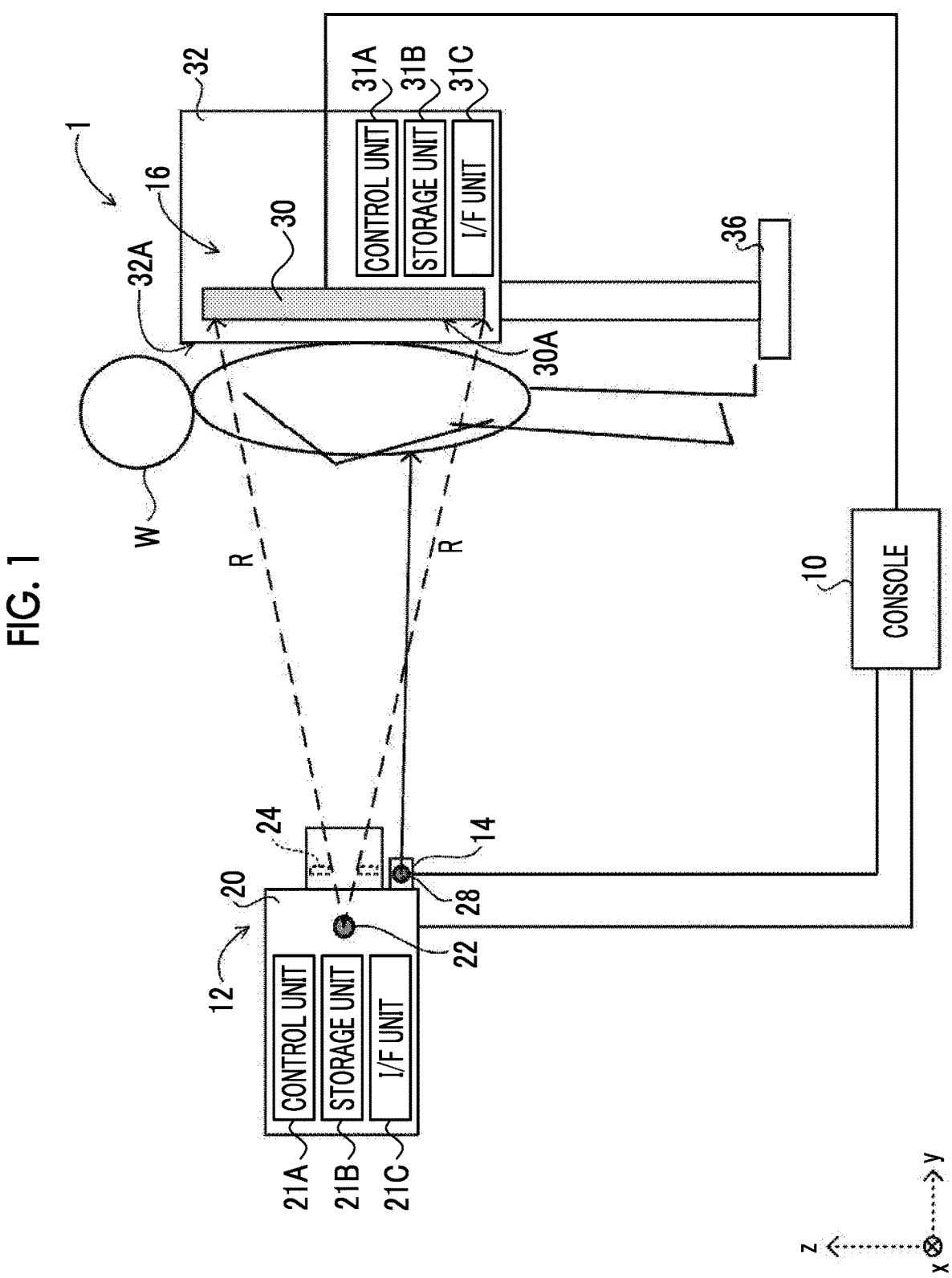
FIG. 1 is a diagram schematically illustrating an example of an overall configuration of a radiography system according to an embodiment.

First, an example of an overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a console 10, a radiation emitting device 12, a time-of-flight (TOF) camera 14, and a radiography apparatus 16. The console 10 according to this embodiment is an example of a setting device according to the present disclosure. In addition, FIG. 1 illustrates an aspect in which a radiographic image is captured in a state in which a subject W is standing up (standing state). However, the state of the subject W is not limited. For example, the subject W may be in a state (sitting state) in which it is sitting on a chair including a wheelchair or in a state in which it lies on an imaging table 32 (lying state).

The radiation emitting device 12 according to this embodiment comprises a radiation source 20 that irradiates the subject W, which is an example of an object to be imaged, with radiation R, such as X-rays, and a collimator 24 that limits an irradiation field of the radiation R emitted from the radiation source 20. In addition, the radiation emitting device 12 comprises a control unit 21A, a storage unit 21B, and an interface (I/F) unit 21C.

The control unit 21A controls the radiation source 20 and the collimator 24 under the control of the console 10. The control unit 21A comprises a central processing unit (CPU), a read only memory (ROM), and a random access memory (RAM) which are not illustrated. Various programs, which include an irradiation processing program for causing the radiation source 20 to irradiate the subject W with the radiation R in the capture of a radiographic image and are executed by the CPU, are stored in the ROM in advance. The RAM temporarily stores various types of data.

For example, various types of information are stored in the storage unit 21B. Specific examples of the storage unit 21B include a hard disk drive (HDD) and a solid state drive (SSD). The I/F unit 21C transmits and receives various types of information to and from the console 10 using wireless communication or wired communication. The irradiation emitting device 12 receives imaging conditions (which will be described in detail below) derived by the console 10 through the I/F unit 21C.

A method by which a user, such as a doctor or a technician, instructs the radiation emitting device 12 to emit the radiation R is not limited. For example, in a case in which the radiation emitting device 12 comprises an irradiation button or the like, the user, such as a radiology technician, may input an instruction to emit the radiation R with the irradiation button such that the radiation R is emitted from the radiation emitting device 12. Further, for example, the user, such as the radiology technician, may operate the console 10 to input the instruction to emit the radiation R such that the radiation R is emitted from the radiation emitting device 12.

In a case in which the radiation emitting device 12 receives the instruction to emit the radiation R, the control unit 21A directs the radiation source 20 to emit the radiation R from a focus 22 of a radiation tube according to the imaging conditions, such as a tube voltage, a tube current, and an irradiation time, set by the console 10. For example, in this embodiment, the irradiation field has a rectangular shape. Therefore, a rectangular-pyramid-shaped region that has the focus 22 as the apex and the irradiation field as the base is irradiated with the radiation R emitted from the focus 22.

Further, as illustrated in FIG. 1, the TOF camera 14 is provided in the vicinity of an exit port through which the radiation R is emitted from the radiation emitting device 12. The TOF camera 14 is a camera that captures a distance image indicating a distance to the object to be imaged using the TOF method with an imaging element 28. Specifically, the TOF camera 14 irradiates the object to be imaged with light, such as infrared rays, and measures the distance between the TOF camera 14 and the object to be imaged on the basis of the time until reflected light is received or a phase change between the emitted light and the received light. In the distance image captured by the TOF camera 14, each pixel has distance information indicating the distance between the TOF camera 14 and the object to be imaged. In addition, in the TOF camera 14 according to this embodiment, the distance between the imaging element 28 and the object to be imaged is applied as the distance between the TOF camera 14 and the object to be imaged. Further, the distance image is an image from which the distance to the object to be imaged can be derived.

The radiography apparatus 16 comprises a radiation detector 30, a control unit 31A, a storage unit 31B, and an I/F unit 31C.

The radiation detector 30 has a function of generating a radiographic image. As illustrated in FIG. 1, the radiation detector 30 is disposed in the imaging table 32. In the radiography apparatus 16 according to this embodiment, in a case in which imaging is performed, the subject W is positioned on an imaging surface 32A of the imaging table 32 by the user.

The radiation detector 30 detects the radiation R transmitted through the subject W and the imaging table 32, generates a radiographic image on the basis of the detected radiation R, and outputs image data indicating the generated radiographic image. The type of the radiation detector 30 according to this embodiment is not particularly limited. For example, the radiation detector 30 may be a radiation detector that uses thallium activated cesium iodide (CsI:Tl) as a scintillator converting the radiation R into light or a radiation detector that uses terbium-activated gadolinium oxysulfide (GOS) $(Gd_2O_2S:Tb)$ as the scintillator. Further, for example, the radiation detector 30 may be a computed radiography (CR) detector. In addition, for example, the radiation detector 30 may be an indirect-conversion-type radiation detector that converts the radiation R into light using a scintillator and the like and converts the converted light into charge or a direct-conversion-type radiation detector that directly converts the radiation R into charge.

The control unit 31A controls the overall operation of the radiography apparatus 16 under the control of the console 10. The control unit 31A comprises a CPU, a ROM, and a RAM which are not illustrated. For example, various programs, which include an imaging processing program for performing control related to the capture of radiographic images and are executed by the CPU, are stored in the ROM in advance. The RAM temporarily stores various types of data.

For example, the image data of the radiographic image captured by the radiation detector 30 and various other types of information are stored in the storage unit 31B. An HDD or an SSD is given as a specific example of the storage unit 31B. The I/F unit 31C transmits and receives various types of information to and from the console 10 using wireless communication or wired communication. The image data of the radiographic image captured by the radiation detector 30 is transmitted to the console 10 through the I/F unit 31C by wireless communication or wired communication.

Meanwhile, the console 10 according to this embodiment has a function of controlling the radiation emitting device 12, the TOF camera 14, and the radiography apparatus 16 using, for example, an imaging order and various types of information acquired from a radiology information system (RIS) (not illustrated), a hospital information system (HIS), and the like through a wireless communication local area network (LAN) or the like.

Figure 2:
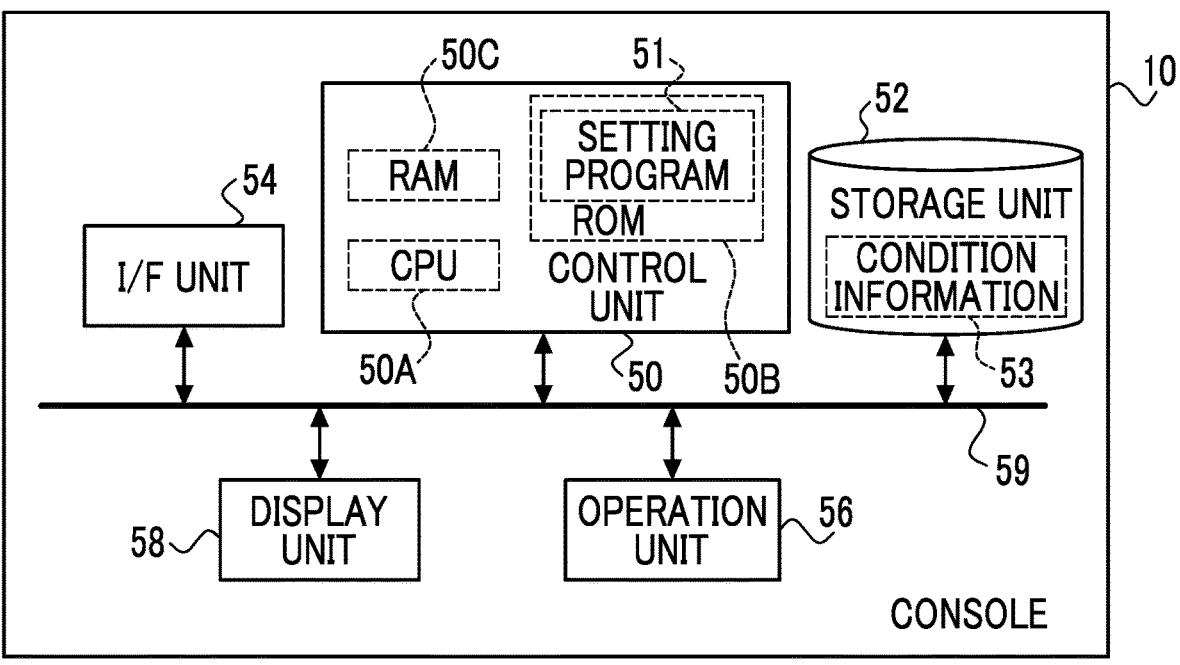
FIG. 2 is a block diagram illustrating an example of a configuration of a console according to the embodiment.

For example, the console 10 according to this embodiment is a server computer. As illustrated in FIG. 2, the console 10 comprises a control unit 50, a storage unit 52, an I/F unit 54, an operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various types of information.

The control unit 50 according to this embodiment controls the overall operation of the console 10. The control unit 50 comprises a CPU 50A, a ROM 50B, and a RAM 50C. For example, various programs including a setting program 51 executed by the CPU 50A are stored in the ROM 50B in advance. The RAM 50C temporarily stores various types of data. The CPU 50A according to this embodiment is an example of a processor according to the present disclosure. In addition, the setting program 51 according to this embodiment is an example of a setting program according to the present disclosure.

For example, the image data of the radiographic image captured by the radiography apparatus 16 and various types of information including the imaging order acquired from the RIS are stored in the storage unit 52. In addition, the storage unit 52 stores condition information 53 which will be described in detail below. An HDD or an SSD is given as a specific example of the storage unit 52.

The operation unit 56 is used by the user to designate an imaging menu corresponding to an imaging order and to input instructions related to the capture of a radiographic image including an instruction to emit the radiation R, various types of information, and the like. The operation unit 56 is not particularly limited. Examples of the operation unit 56 include various switches, a touch panel, a touch pen, and a mouse. The display unit 58 is used to display various types of information. In addition, the operation unit 56 and the display unit 58 may be integrated into a touch panel display.

The console 10 displays a plurality of types of imaging menus prepared in advance on the display unit 58 such that one of the menus can be selected. The user selects one imaging menu that is matched with the content of the imaging order through the operation unit 56. In this embodiment, the imaging menu is predetermined for each of imaging parts, such as the head, the chest, the abdomen, and the spine, and the user selects an imaging part to select an imaging menu. Therefore, the console 10 receives the designation of the imaging menu.

The I/F unit 54 transmits and receives various types of information to and from the radiography apparatus 16 and the RIS (not illustrated) using wireless communication or wired communication. In the radiography system 1 according to this embodiment, the console 10 receives the image data of the radiographic image captured by the radiography apparatus 16 from the radiography apparatus 16 through the I/F unit 54, using wireless communication or wired communication.

Figure 3:
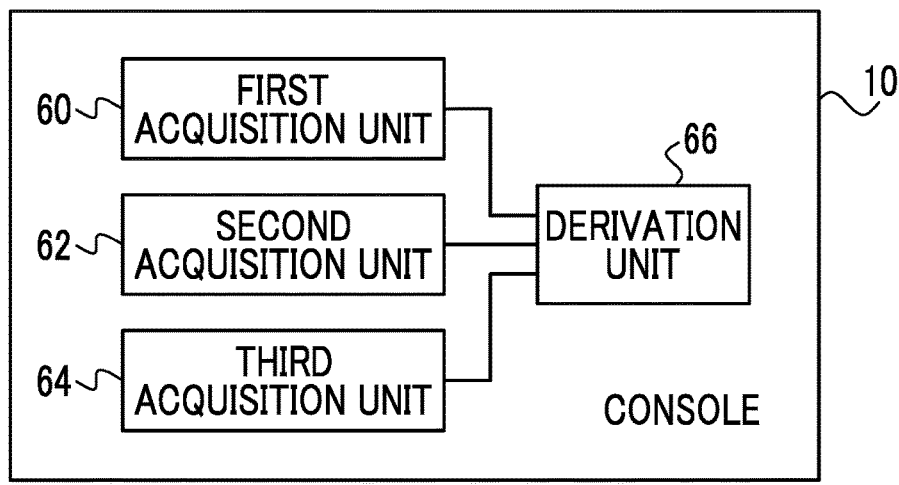
FIG. 3 is a functional block diagram illustrating an example of a functional configuration of the console according to the embodiment.

In addition, FIG. 3 is a functional block diagram illustrating an example of the functional configuration of the console 10 according to this embodiment. As illustrated in FIG. 3, the console 10 comprises a first acquisition unit 60, a second acquisition unit 62, a third acquisition unit 64, and a derivation unit 66. For example, in the console 10 according to this embodiment, the CPU 50A of the control unit 50 executes the setting program 51 stored in the ROM 50B to function as the first acquisition unit 60, the second acquisition unit 62, the third acquisition unit 64, and the derivation unit 66.

The first acquisition unit 60 has a function of acquiring imaging part information indicating an imaging part of the subject W. For example, in this embodiment, the imaging part information is acquired from the received imaging menu. In addition, the method by which the first acquisition unit 60 acquires the imaging part information is not particularly limited. For example, in a case in which the imaging part information is included in the imaging order, the imaging part information may be acquired from the imaging order. The imaging part information acquired by the first acquisition unit 60 is output to the derivation unit 66.

The second acquisition unit 62 has a function of acquiring body thickness information indicating a body thickness of the subject W in a direction in which the radiation R is transmitted. In addition, in this embodiment, the term "body thickness" means a body thickness of the subject W in the direction in which the radiation R is transmitted. For example, the second acquisition unit 62 according to this embodiment acquires the distance image captured by the TOF camera 14 and derives the body thickness from the acquired distance image to acquire the body thickness information. For example, the second acquisition unit 62 according to this embodiment acquires image data indicating the distance image captured by the TOF camera 14 from the TOF camera 14 through the I/F unit 31C and the I/F unit 54. Then, the second acquisition unit 62 derives the body thickness on the basis of the acquired distance image to acquire the body thickness information. The body thickness information acquired by the second acquisition unit 62 is output to the derivation unit 66.

An example of a method for deriving the body thickness will be described with reference to FIG. 4.

As described above, in this embodiment, the body thickness is derived from the distance image captured by the TOF camera 14. The TOF camera 14 measures a distance between the TOF camera 14 and an object to be measured. As illustrated in FIGS. 1 and 4, in this embodiment, since the position of the imaging element 28 of the TOF camera 14 is different from the position of the focus 22 of the radiation source 20, the distance to the object to be measured which has been measured by the TOF camera 14 is different from the distance between the radiation source 20 and the object to be measured. In the radiography system 1 according to this embodiment, a relative positional relationship between the TOF camera 14 and the radiation source 20 is predetermined. Therefore, a conversion coefficient for converting the distance to the object to be measured, which has been measured by the TOF camera 14, into the distance between the radiation source 20 and the object to be measured is stored in advance in the storage unit 52 of the console 10.

Figure 4:
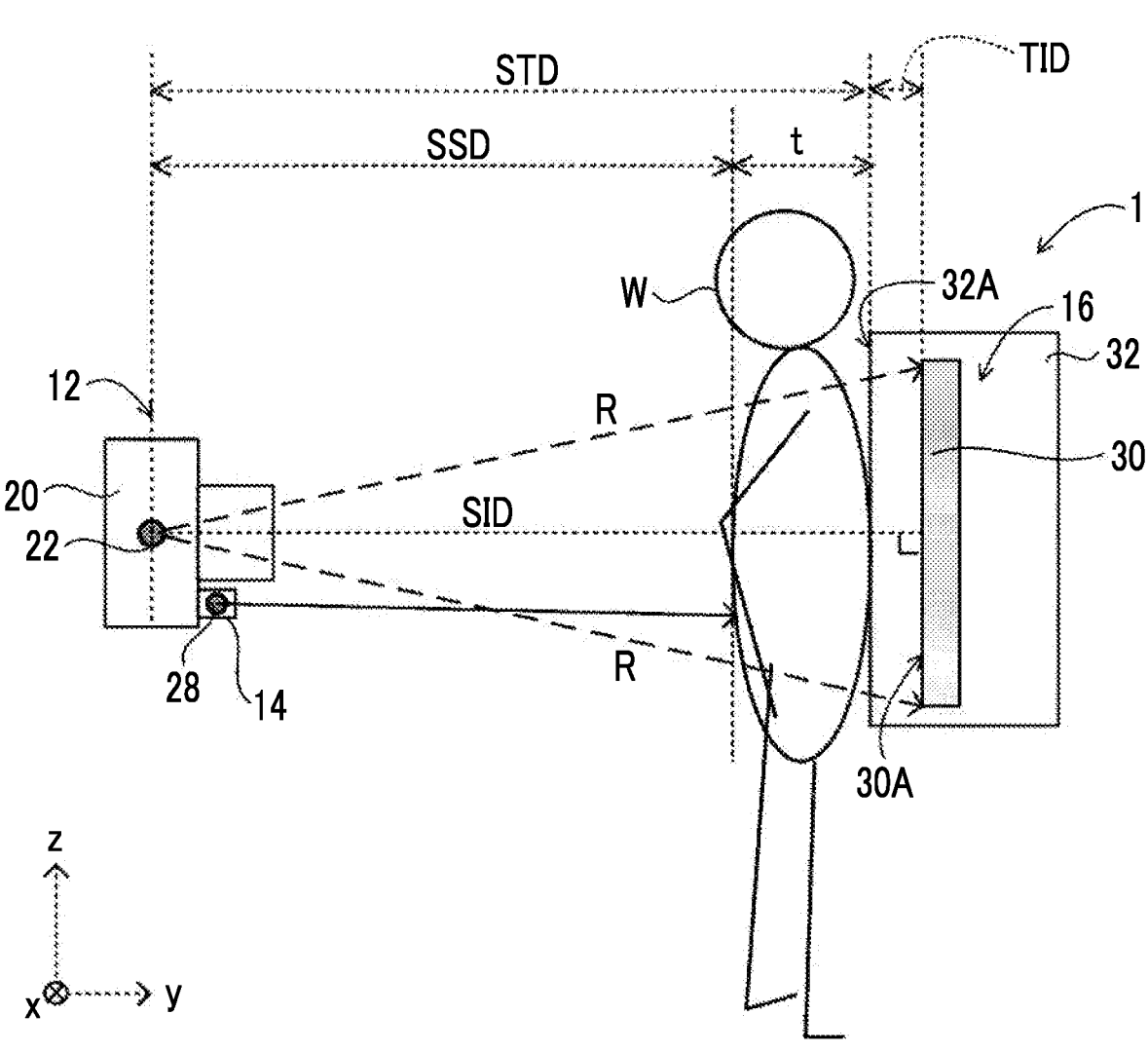
FIG. 4 is a diagram illustrating a method for acquiring a body thickness.

As illustrated in FIG. 4, the second acquisition unit 62 according to this embodiment derives a body thickness t using the following Expression (1) on the basis of a source target distance (STD) and a source-to-skin distance (SSD).

$$t = STD - SSD \tag{1}$$

The STD is a distance between the radiation source 20 and a target (object to be imaged). In this embodiment, as illustrated in FIG. 4, the STD means a distance between the focus 22 of the radiation source 20 and the imaging surface 32A of the imaging table 32. Specifically, the STD means the length of a perpendicular line drawn from the focus 22 of the radiation source 20 to the imaging surface 32A of the imaging table 32.

Specifically, the position of the imaging surface 32A of the imaging table 32 which is not hidden by the subject W is predetermined as a measurement position in order to derive the STD. The second acquisition unit 62 derives the distance between the TOF camera 14 and the measurement position from distance information included in a pixel which corresponds to the measurement position in the distance image. Further, in a case in which the measurement position is different from the foot of the perpendicular line drawn from the TOF camera 14 to the imaging surface 32A of the imaging table 32, the second acquisition unit 62 converts the derived distance between the TOF camera 14 and the measurement position into the length of the perpendicular line drawn from the TOF camera 14 to the imaging surface 32A of the imaging table 32. Furthermore, the second acquisition unit 62 derives the STD by converting the distance between the TOF camera 14 and the imaging surface 32A of the imaging table 32 into the distance between the radiation source 20 and the imaging surface 32A of the imaging table 32, using a conversion coefficient for deriving the STD among the conversion coefficients stored in the storage unit 52.

In addition, in a case in which the STD is predetermined and is, for example, a fixed value corresponding to the imaging part, the STD may be stored in the storage unit 52 in advance, and the second acquisition unit 62 may acquire the STD from the storage unit 52.

Further, the SSD is the distance between the radiation source 20 and the surface (skin) of the subject W, that is, a distance from the radiation source 20 to the subject W. In this embodiment, the SSD means the distance from the focus 22 of the radiation source 20 to the body surface of the subject W facing the focus 22 as illustrated in FIG. 4. Specifically, the SSD means the length of a perpendicular line drawn from the focus 22 of the radiation source 20 to the subject W.

More specifically, the second acquisition unit 62 derives the distance between the TOF camera 14 and the subject W from the distance information included in the pixels corresponding to the subject W in the distance image captured by the TOF camera 14. Further, the second acquisition unit 62 derives the SSD by converting the distance between the TOF camera 14 and the subject W into the distance between the radiation source 20 and the subject W, using a conversion coefficient for deriving the SSD among the conversion coefficients stored in the storage unit 52.

In addition, the method by which the second acquisition unit 62 derives the body thickness t is not limited to the above-described method. For example, the second acquisition unit 62 may derive the body thickness t using the following Expression (2) on the basis of a source-to-image receptor distance (SID), the SSD, and a target-to-image receptor distance (TID).

$$t = SID - SSD - TID \tag{2}$$

The SID is the distance between the radiation source 20 and the radiation detector 30. Further, in this embodiment, the SID means the length of a perpendicular line drawn from the focus 22 of the radiation source 20 to a detection surface 30A of the radiation detector 30 as illustrated in FIG. 4. For example, in this embodiment, the SID is a fixed value predetermined according to the imaging part and is stored in the storage unit 52 in advance. Therefore, the second acquisition unit 62 acquires the SID from the storage unit 52.

In addition, unlike this embodiment, the SID may be measured whenever a radiographic image is captured. In this case, for example, the second acquisition unit 62 may acquire a measurement result of the SID by a measurement device such as a linear encoder.

Further, the TID is the distance between the target (object to be imaged) and the radiation detector 30. In this embodiment, the TID means the distance from the detection surface 30A of the radiation detector 30 to the imaging surface 32A of the imaging table 32. For example, in this embodiment, the TID is a fixed value, is predetermined as a design value of the imaging table 32, and is stored in the storage unit 52 in advance. Therefore, the second acquisition unit 62 acquires the TID from the storage unit 52.

The third acquisition unit 64 has a function of acquiring condition information indicating the imaging conditions set in the radiation emitting device 12. The dose of the radiation R transmitted through the subject W varies depending on the body thickness t of the subject W. For example, in a case in which the imaging part of the subject W is the same, the dose of the radiation R transmitted through the subject W is lower as the thickness of the subject W is larger. In the radiography system 1 according to this embodiment, control is performed such that the dose of the radiation transmitted through the subject W is the same regardless of the body thickness t of the subject W. Specifically, the radiation R is emitted such that the dose of the radiation R transmitted through the imaging part of the subject W is the same as a dose at a reference body thickness t_c. In addition, the term "same" is not limited to "exact same" and may have, for example, an error in an allowable range.

Therefore, in the radiation emitting device 12 according to this embodiment, the dose for the body thickness t of the subject W is set. Specifically, any one of the following three conditions is set as an imaging condition related to the tube voltage value and the mAs value of the radiation source 20.

A first condition is a condition in which the tube voltage value is set to a fixed value regardless of the body thickness t of the subject W and the mAs value is set to a variable value corresponding to the body thickness t of the subject W. Specifically, in a case in which the first condition is set, for the tube voltage value, a tube voltage value corresponding to the reference body thickness t_c is used as the fixed value. On the other hand, the mAs value is a variable value that corresponds to the body thickness t of the subject W and is larger as the body thickness t is larger.

A second condition is a condition in which the tube voltage value is a variable value corresponding to the body thickness t of the subject W and the mAs value is a fixed value regardless of the body thickness t of the subject W. Specifically, in a case in which the second condition is set, the tube voltage value is a variable value that corresponds to the body thickness t of the subject W and is larger as the body thickness t is larger. On the other hand, for the mAs value, a mAs value corresponding to the reference body thickness t_c, specifically, the current value mA of the tube current and the irradiation time msec of the radiation R are used as fixed values.

A third condition is a condition in which the tube voltage value is a variable value corresponding to the body thickness t of the subject W and the mAs value is a variable value corresponding to the body thickness t of the subject W. Specifically, in a case in which the third condition is set, as the body thickness t of the subject W is larger, at least one of the tube voltage value or the mAs value is larger.

In a case in which the tube voltage value is a variable value corresponding to the body thickness t of the subject W, the tube voltage value is increased in order to suppress an increase in contrast due to the widening of the range of a histogram of the radiation R transmitted through the subject W which is caused by an increase in the body thickness t. It can be expected that the radiographic image will be adjusted to a constant contrast with respect to a change in the body thickness t by increasing the tube voltage value in this way.

Further, since the mAs value, that is, the current value mA of the tube current and the irradiation time msec of the radiation R are set as fixed values regardless of the body thickness t, the stability of image quality for heartbeat and body movement is maintained even in a case in which the body thickness t changes depending on the subject W. In addition, in a case in which the focus size increases, the radiographic image is likely to be blurred. However, the mAs value is set to a fixed value, which makes it possible to keep the focus size of the radiation source 20 constant as a small focus. Therefore, it can be expected that the sharpness of the radiographic image will be stabilized.

Since each of the first to third conditions has its own characteristics, which of the first to third conditions is set as the imaging condition in the radiation emitting device 12 may depend on, for example, the facility in which the radiography system 1 is installed. In addition, in a case in which the quality of the radiation R for the body thickness t, that is, the condition of the tube voltage is converted, for example, the quality of the captured radiographic image is changed. Therefore, even for the same subject W, it may be difficult to compare a past radiographic image with a current radiographic image. For this reason, it is preferable to inherit the setting of which of the first to third conditions is set for each imaging environment in which the same subject W is imaged, for example, for each facility in which the radiography system 1 is installed.

For example, in the radiography system 1 according to this embodiment, any one of the first to third conditions is preset as the imaging condition in the console 10. Specifically, as illustrated in FIG. 2, the condition information 53 indicating which of the first to third conditions is set as imaging condition is stored in the storage unit 52 of the console 10. Therefore, the third acquisition unit 64 has a function of acquiring the condition information indicating the imaging condition from the storage unit 52. The condition information acquired by the third acquisition unit 64 is output to the derivation unit 66. In addition, the setting destination of the imaging condition is not limited to the console 10 and may be, for example, the radiation emitting device 12. Further, a method for setting any one of the first to third conditions as the imaging condition is not limited. For example, the imaging condition may be set by the user or may be set by a person who performs the maintenance of the radiography system 1.

The derivation unit 66 has a function of deriving the set value of the tube voltage and the set value of the mAs value of the radiation emitting device 12 for emitting the radiation R such that the dose of the radiation transmitted through the imaging part of the subject W is the same as the dose at the reference body thickness t_c, on the basis of the imaging part indicated by the imaging part information, the body thickness t indicated by the body thickness information, and the condition indicated by the condition information.

In a case in which the imaging condition set in the radiation emitting device 12 is the third condition, the derivation unit 66 derives the set value of the tube voltage kV corresponding to the body thickness t of the subject W. A method for deriving the set value of the tube voltage kV corresponding to the body thickness t of the subject W in this embodiment will be described with reference to FIG. 5. FIG. 5 is an example of a graph illustrating a correspondence relationship between the body thickness t of the subject W and the set value of the tube voltage kV. In this embodiment, for example, as illustrated in FIG. 5, a correspondence relationship represented by a linear function is established between the body thickness t of the subject W and the set value of the tube voltage kV.

The reference body thickness t_c is the average value of the body thicknesses t of a plurality of subjects W. For example, the reference body thickness t_c is a value that is determined on the basis of at least one of the imaging part, the race of the subject W, the gender of the subject W, the age of the subject W, or the ratio of muscle to fat in the subject W. In this embodiment, information indicating a correspondence relationship between at least one of the imaging part, the race of the subject W, the gender of the subject W, the age of the subject W, or the ratio of muscle to fat in the subject W and the reference body thickness t_c is stored in the storage unit 52 in advance (not illustrated).

A reference tube voltage kV_c is a value that is determined according to, for example, the quality of the captured radiographic image. In addition, the reference tube voltage kV_c may be set by the user. A fluctuation range ΔkV is a fluctuation range of the tube voltage kV with respect to the reference tube voltage kV_c and is a value that is determined according to, for example, the quality of the captured radiographic image. In addition, the fluctuation range ΔkV may be set by the user. Further, as illustrated in FIG. 5, the fluctuation range ΔkV is defined by a magnification x in a case in which the width of the body thickness t is x times a standard deviation σ. Similarly to the reference body thickness t_c, the standard deviation σ of the body thickness t is determined on the basis of at least one of the imaging part, the race of the subject W, the gender of the subject W, the age of the subject W, or the ratio of muscle to fat in the subject W. At least one of the fluctuation range ΔkV or the magnification x can be adjusted to adjust the correspondence relationship between the body thickness t of the subject W and the set value of the tube voltage kV. In addition, in the radiography system 1 according to this embodiment, the fluctuation range and the magnification x are predetermined values and are stored in the storage unit 52 in advance (not illustrated). The reference tube voltage kV_c, the fluctuation range ΔkV, the standard deviation σ, and the magnification x in this embodiment are examples of adjustment information according to the present disclosure.

Therefore, the derivation unit 66 according to this embodiment derives the set value of the tube voltage kV, using the imaging part, the body thickness t of the subject W, the reference tube voltage kV_c, the fluctuation range ΔkV, and the magnification x as parameters, as defined in the following Expression (3).

$$kV = kV(\text{imaging part}, t, kV\_c, \Delta kV, x) \tag{3}$$

The method by which the derivation unit 66 derives the set value of the tube voltage kV corresponding to the body thickness t of the subject W is not limited to the above-described method. In other words, the adjustment information according to the present disclosure is not limited to the above-described aspect. For example, as the correspondence relationship between the body thickness t of the subject W and the set value of the tube voltage kV, a gradient (dkV/dt) of the set value of the tube voltage kV with respect to the body thickness t of the subject W may be defined, and the set value of the tube voltage kV corresponding to the body thickness t of the subject W may be derived using this definition. Further, for example, in a case in which the body thickness t of the subject W and the set value of the tube voltage kV indicate a non-linear correspondence relationship, a table, such as a lookup table (LUT), indicating the correspondence relationship between the body thickness t of the subject W and the set value of the tube voltage kV may be prepared, and the set value of the tube voltage kV corresponding to the body thickness t of the subject W may be derived using this table.

In addition, the derivation unit 66 derives a linear attenuation coefficient ρ corresponding to the set value of the tube voltage kV. A method for deriving the linear attenuation coefficient ρ corresponding to the set value of the tube voltage kV in this embodiment will be described with reference to FIG. 6. FIG. 6 is an example of a graph illustrating a correspondence relationship between the set value of the tube voltage kV and the linear attenuation coefficient ρ.

The linear attenuation coefficient ρ is determined according to the imaging part, the set value of the tube voltage kV, and a filter applied to the radiation source 20. Since gas, blood, muscle, and fat differ depending on the imaging part, the linear attenuation coefficient ρ differs depending on the imaging part. Therefore, in this embodiment, the graph showing the correspondence relationship between the set value of the tube voltage kV and the linear attenuation coefficient ρ illustrated in FIG. 6 is stored in advance in the storage unit 52 for each imaging part (not illustrated). Further, a filter (not illustrated) is added to the radiation source 20, and the subject W is irradiated with the radiation R transmitted through the filter. Examples of the filter include a filter using copper (Cu), a filter using rhodium (Rh), and a filter using aluminum (Al). The filter used for imaging differs depending on, for example, the intended use. The linear attenuation coefficient ρ differs depending on the type (material) of the filter. Further, the linear attenuation coefficient ρ varies depending on the thickness of the filter, specifically, the thickness in the direction in which the radiation R is transmitted. The linear attenuation coefficient ρ is smaller as the thickness of the filter is larger. In other words, the linear attenuation coefficient ρ has a value that differs depending on the conditions (material, thickness, and the like) of the filter added to the radiation source 20. In addition, even in a case in which the set value of the tube voltage kV and the conditions of the filter added to the radiation source 20 are the same, radiation quality may be different for each radiation emitting device 12. Therefore, it is preferable that calibration or the like is performed for each radiation emitting device 12 to adjust the correspondence relationship between the set value of the tube voltage kV and the linear attenuation coefficient ρ.

Therefore, the derivation unit 66 according to this embodiment derives the linear attenuation coefficient ρ corresponding to the set value of the tube voltage kV, using the correspondence relationship between the set value of the tube voltage kV and the linear attenuation coefficient ρ stored in the storage unit 52.

In addition, the derivation unit 66 derives a reference mAs value mAs_c that is used in a case in which a predetermined tube voltage kV at the reference body thickness t_c is applied. The reference mAs value mAs_c corresponds to a target value of the dose of the radiation R transmitted through the imaging part. For example, the reference mAs value mAs_c according to this embodiment is a value that is determined according to the imaging part, the reference tube voltage kV_c, the conditions of the filter, the type of the radiation detector 30, the concentration of automatic exposure control (AEC) in the control of the radiation detector 30, and the SID.

As defined in the following Expression (4), the derivation unit 66 according to this embodiment derives the reference mAs value mAs_c, using the imaging part, the reference tube voltage kV_c, the conditions of the filter, the type of the radiation detector 30, the concentration of the AEC, and the SID as parameters.

$$mAs\_c = A(\text{imaging part}, kV\_c, \text{conditions of filter}) \times$$
$$(\text{current SID/reference value of SID})^2 \times B(\text{type of}$$
$$\text{radiation detector 30}) \times C(\text{concentration of AEC}) \qquad (4)$$

In the above-described Expression (4), "A" is determined on the basis of the reference value of the SID. Therefore, in a case in which the SID in the current measurement of the subject W is different from the reference value of the SID, "A" is corrected by integrating (current SID/reference value of SID)$^2$ as illustrated in the above-described Expression (4). In addition, in a case in which the reference tube voltage kV_c differs, the reference mAs value mAs_c to be set differs even though the imaging part is the same. Further, the reference mAs value mAs_c to be set differs in a case in which the conditions of the filter applied to the radiation source 20 differs.

Meanwhile, in the above-described Expression (4), "B" is a parameter for adjusting the reference mAs value mAs_c and is a dose ratio corresponding to the type of the radiation detector 30. An example of a method for deriving "B" is a method that measures noise equivalent quanta (NEQ) while changing a dose with the corresponding radiation quality for each type of radiation detector 30 and compares the doses for achieving the same NEQ for each type of radiation detector 30 to derive a dose ratio. In addition, another example of the method is a method that visually evaluates a radiographic image obtained by imaging a contrast detail radiography (CDRAD) phantom while changing a dose with the corresponding radiation quality, derives IQFinv which is an index for quantifying total image quality including contrast and granularity, and compares the doses for achieving the same IQFinv for each type of radiation detector 30 to derive a dose ratio.

FIG. 7 illustrates an example of correspondence relationship information (hereinafter, referred to as "dose ratio information") indicating a correspondence relationship between the type of the radiation detector 30 and the dose ratio. In the example of the dose ratio information illustrated in FIG. 7, in a case in which a dose for the radiation detector 30, which is a type using GOS as the scintillator, is used as a standard (a dose ratio B=1.0), the dose ratios B for other types of radiation detectors 30 are illustrated. For example, in this embodiment, dose ratio information 70 is stored in the storage unit 52 in advance.

Meanwhile, in the above-described Expression (4), "C" is a parameter for adjusting the reference mAs value mAs_c and corresponds to the concentration of the AEC in the control of the radiation detector 30.

As in the setting of the concentration of the AEC, for example, "C" is stored in advance in the storage unit 52 as a ±3-step adjustment value, such as 0.58, 0.69, 0.83, 1.0, 1.2, 1.4, and 1.7, for every ±20% (not illustrated).

In addition, the derivation unit 66 corrects the reference mAs value mAs_c according to the difference between the body thickness t of the subject W and the reference body thickness t_c to derive the set value of the mAs value corresponding to the body thickness t of the subject W. Specifically, the derivation unit 66 derives the set value of the mAs value corresponding to the body thickness t of the subject W using the following Expression (5).

$$mAs \text{ value} = mAs\_c \times \exp(\rho \times (t - t\_c)) \qquad (5)$$

In the above-described Expression (5), "mAs_c" is the reference mAs value and is derived by the above-described method. In addition, "ρ" is a linear attenuation coefficient and is derived by the above-described method.

In a case in which the imaging condition set in the radiation emitting device 12 is the third condition, the derivation unit 66 derives the set value of the tube voltage kV corresponding to the body thickness t of the subject W in this way.

On the other hand, in a case in which the imaging condition set in the radiation emitting device 12 is the first condition, the set value of the tube voltage kV is a fixed value regardless of the body thickness t of the subject W and is the reference tube voltage kV_c. Therefore, in the case of the third condition, the fluctuation range ΔkV may be set to zero (ΔkV=0) and can be derived by the same method as in the first condition.

On the other hand, in a case in which the imaging condition set in the radiation emitting device 12 is the second condition, the set value of the mAs value is a fixed value regardless of the body thickness t of the subject W and is the reference mAs value mAs_c. Meanwhile, the set value of the tube voltage kV is derived according to at least one of the body thickness t of the subject W, the imaging part, the reference tube voltage kV_c, or the filter added to the radiation source 20 in order to make the dose of the radiation transmitted through the imaging part the same as the dose at the reference body thickness t_c. Specifically, the derivation unit 66 derives the set value of the tube voltage kV, using the imaging part, the body thickness t of the subject W, the reference tube voltage kV_c, and the filter added to the radiation source 20 as parameters, as defined in the following Expression (6).

$$kV = kV(\text{imaging part}, t, kV\_c, \text{conditions of filter}) \qquad (6)$$

For example, in this embodiment, a table (not illustrated), such as an LUT, showing the correspondence relationship among the set value of the tube voltage kV, the body thickness t, the reference tube voltage kV_c, and the conditions of the filter is stored for each imaging part in the storage unit 52 in advance. The derivation unit 66 derives the set value of the tube voltage kV corresponding to the body thickness t of the subject W and each parameter with reference to the table corresponding to the imaging part which is stored in the storage unit 52.

Next, the operation of the console 10 according to this embodiment will be described with reference to the drawings.

Figure 8:
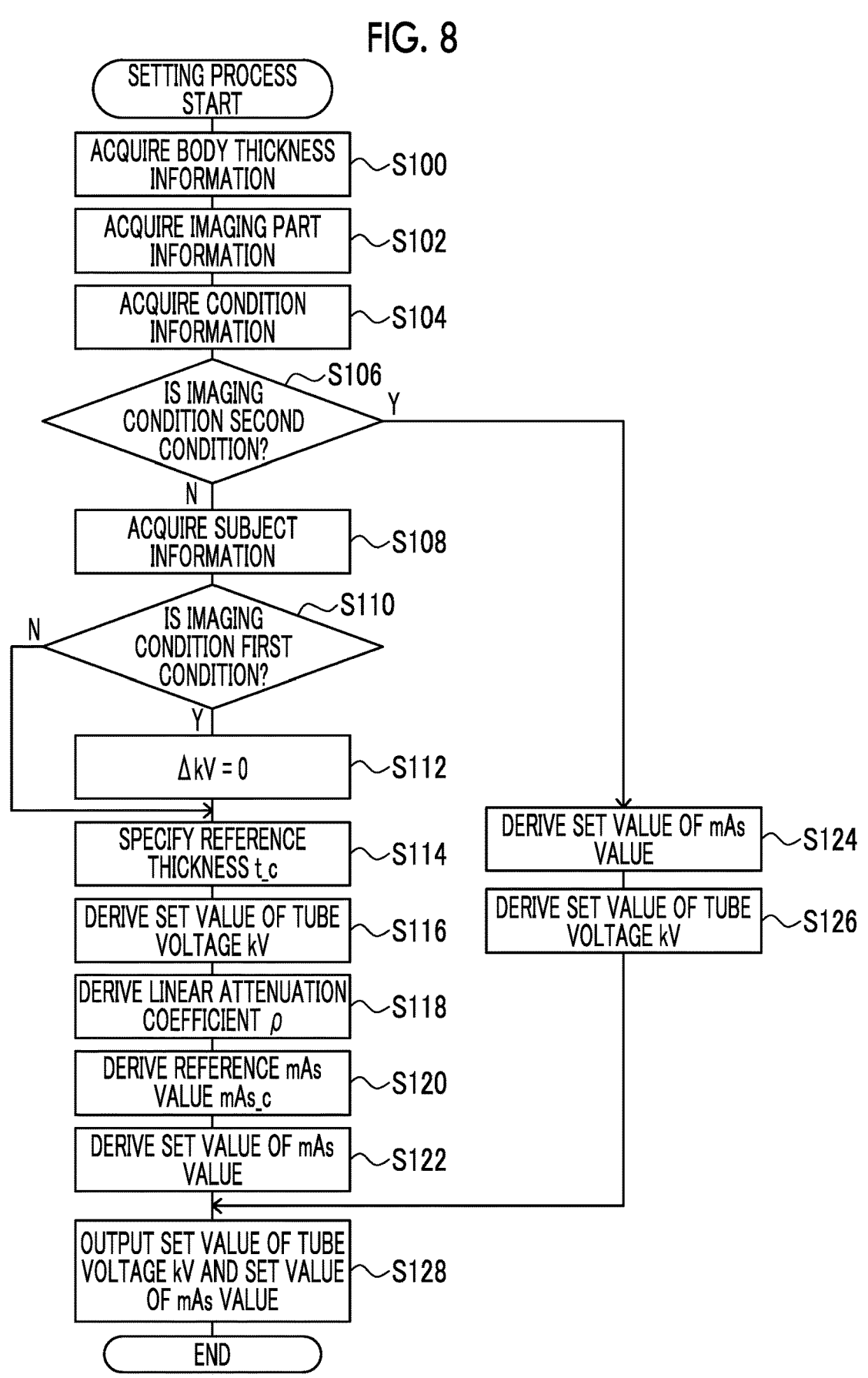
FIG. 8 is a flowchart illustrating an example of a flow of a setting process of the console according to the embodiment.

In the console 10 according to this embodiment, the CPU 50A of the control unit 50 executes the setting program 51 stored in the ROM 50B to perform a setting process whose example is illustrated in FIG. 8. FIG. 8 is a flowchart illustrating an example of the flow of the setting process performed in the console 10 according to this embodiment. In addition, the timing when the CPU 50A performs the setting process is not limited, and the CPU 50A may perform the setting process at any timing. For example, the setting process may be performed at the timing when an instruction input from the user by the operation of the operation unit 56 after the positioning of the subject W ends is received or the timing when an instruction to emit the radiation R is received from the user.

Then, in Step S100 of FIG. 8, the second acquisition unit 62 acquires the body thickness information as described above. Specifically, the second acquisition unit 62 instructs the TOF camera 14 to capture a distance image and acquires the distance image captured by the TOF camera 14 on the basis of the instruction through the I/F unit 54. The second acquisition unit 62 acquires the body thickness information from the acquired distance image using the above-described Expression (1) or (2).

Then, in Step S102, the first acquisition unit 60 acquires the imaging part information from the imaging menu as described above. Then, in Step S104, the third acquisition unit 64 acquires the condition information 53 from the storage unit 52 as described above.

Then, in Step S106, the derivation unit 66 determines whether or not the imaging condition indicated by the condition information acquired in Step S104 is the second condition. In a case in which the imaging condition indicated by the acquired condition information is not the second condition, that is, in a case in which the imaging condition indicated by the acquired condition information is the first condition or the third condition, the determination result in Step S106 is "No", and the process proceeds to Step S108.

In Step S108, the derivation unit 66 acquires subject information related to the subject W. The subject information acquired in this step is information which is a parameter necessary for deriving the reference body thickness t_c and the standard deviation σ of the body thickness t. For example, in this embodiment, as described above, the race, gender, and age of the subject W and the ratio of muscle to fat in the subject W are acquired. In addition, the method by which the derivation unit 66 acquires the subject information is not particularly limited.

As the method by which the derivation unit 66 acquires the gender and the age as the subject information, for example, the gender and the age may be acquired from the HIS, the RIS, or the like. In a case in which the subject information is included in the imaging order, the gender and the age may be acquired from the imaging order. In addition, for example, the derivation unit 66 may acquire information indicating the gender and the age input by the user using the operation unit 56.

Further, as the method by which the derivation unit 66 acquires the race as the subject information, for example, the race of the subject may be determined from a visible light image obtained by imaging the subject W with a visible light camera. In this case, a race determination trained model for determining the race of the subject W from the visible light image may be used. Specifically, a race determination trained model may be used which is generated using a plurality of learning information items in which racial information indicating the race of the object to be imaged is associated with visible light images obtained by imaging persons of various races, receives a visible light image obtained by imaging the subject W as an input, and outputs racial information indicating the race of the object to be imaged. A neural network model is given an example of the race determination trained model. For example, a back-propagation method can be applied as a learning algorithm. The derivation unit 66 can acquire the race as the subject information by inputting the visible light image obtained by imaging the subject W to the race determination trained model and obtaining racial information from the race determination trained model. In addition, for example, the derivation unit 66 may acquire information indicating the race input by the user using the operation unit 56.

Further, as the method by which the derivation unit 66 acquires the ratio of muscle to fat as the subject information, for example, the ratio of muscle to fat in the subject may be determined from a visible light image obtained by imaging the subject W with a visible light camera. In this case, a ratio determination trained model for determining the ratio of muscle to fat in the subject W from the visible light image may be used. Specifically, a ratio determination trained model may be used which is generated using a plurality of learning information items in which the ratios of muscle to fat in the objects to be imaged are associated with visible light images obtained by imaging persons having various ratios of muscle to fat, receives a visible light image obtained by imaging the subject W as an input, and outputs ratio information indicating the ratio of muscle to fat in the object to be imaged. A neural network model is given an example of the ratio determination trained model. For example, the back-propagation method can be applied as the learning algorithm. The derivation unit 66 can acquire the ratio of muscle to fat as the subject information by inputting the visible light image obtained by imaging the subject W to the ratio determination trained model and obtaining ratio information from the ratio determination trained model. Further, for example, the derivation unit 66 may derive an index, such as a body mass index (BMI), from the height and weight of the subject W and acquire the ratio of muscle to fat in the subject W from the derived index. In this case, the height and weight of the subject W may be acquired from, for example, the HIS or the RIS. In addition, for example, the derivation unit 66 may acquire information indicating the ratio of muscle to fat input by the user using the operation unit 56.

Then, in Step S110, the derivation unit 66 determines whether or not the imaging condition indicated by the condition information acquired in Step S104 is the first condition. In a case in which the imaging condition indicated by the acquired condition information is the first condition, the determination result in Step S110 is "Yes", and the process proceeds to Step S112.

In Step S112, the derivation unit 66 sets the fluctuation range ΔkV of the tube voltage kV to zero (ΔkV=0) and then proceeds to Step S114. As described above, in a case in which the imaging condition set in the radiation emitting device 12 is the first condition, the fluctuation range ΔkV is set to zero since the tube voltage kV is a fixed value.

On the other hand, in a case in which the imaging condition indicated by the condition information acquired in Step S104 is not the first condition in Step S110, that is, in a case in which the imaging condition indicated by the acquired condition information is the third condition, the determination result in Step S110 is "No", and the process proceeds to Step S114.

In Step S114, the derivation unit 66 specifies the reference body thickness t_c of the subject W. As described above, the reference body thickness t_c is a value that is determined on the basis of at least one of the imaging part, the race of the subject W, the gender of the subject W, the age of the subject W, or the ratio of muscle to fat in the subject W. Therefore, the derivation unit 66 specifies the reference body thickness t_c of the subject W, using the subject information acquired in Step S108.

Then, in Step S116, the derivation unit 66 derives the set value of the tube voltage kV corresponding to the body thickness t of the subject W as described above. Specifically, the derivation unit 66 derives the set value of the tube voltage kV on the basis of the definition of the above-described Expression (3), using the subject information acquired in Step S108.

Then, in Step S118, the derivation unit 66 derives the linear attenuation coefficient ρ corresponding to the set value of the tube voltage kV as described above. Specifically, the derivation unit 66 derives the linear attenuation coefficient ρ corresponding to the set value of the tube voltage kV, using the correspondence relationship between the set value of the tube voltage kV and the linear attenuation coefficient ρ stored in the storage unit 52.

Then, in Step S120, the derivation unit 66 derives the reference mAs value mAs_c as described above. Specifically, the derivation unit 66 derives the reference mAs value mAs_c on the basis of the definition of the above-described Expression (4).

Then, in Step S122, the derivation unit 66 derives the set value of the mAs value as described above and then proceeds to Step S128. Specifically, the set value of the mAs value is derived on the basis of the definition of the above-described Expression (5), using the reference body thickness t_c specified in Step S114, the linear attenuation coefficient ρ derived in Step S118, and the reference mAs value mAs_c derived in Step S120.

On the other hand, in a case in which the imaging condition indicated by the condition information acquired in Step S104 is the second condition in Step S106, the determination result in Step S106 is "Yes", and the process proceeds to Step S124.

Then, in Step S124, the derivation unit 66 derives the set value of the mAs value as described above. Specifically, the reference mAs value mAs_c is derived as the set value of the mAs value.

Then, in Step S126, the derivation unit 66 derives the set value of the tube voltage kV as described above and then proceeds to Step S128. Specifically, the derivation unit 66 derives the set value of the tube voltage kV corresponding to the body thickness t of the subject W and each parameter on the basis of the definition of the above-described Expression (6), with reference to the table corresponding to the imaging part stored in the storage unit 52.

In Step S128, the derivation unit 66 outputs the set value of the tube voltage kV and the set value of the mAs value to the radiation emitting device 12 through the I/F unit 54. Then, in the radiation emitting device 12, the tube voltage kV and the mAs value for emitting the radiation R are set. In a case in which the process in Step S128 ends, the setting process illustrated in FIG. 8 ends.

As described above, the console 10 according to each of the above-described embodiments comprises the CPU 50A as at least one processor. The CPU 50A acquires the imaging part information indicating the imaging part of the subject W whose radiographic image is captured by the radiation R emitted from the radiation emitting device 12. In addition, the CPU 50A acquires the body thickness information indicating the body thickness t of the subject W in the direction in which the radiation R is transmitted. Further, the CPU 50A acquires the condition information indicating whether the imaging condition set in the radiation emitting device 12 is the first condition in which the tube voltage value is a fixed value and the mAs value is a variable value, the second condition in which the tube voltage value is a variable value and the mAs value is a fixed value, or the third condition in which the tube voltage value is a variable value and the mAs value is a variable value. In addition, the CPU 50A derives the set values of the tube voltage and the mAs value of the radiation emitting device 12 for emitting the radiation R such that the dose of the radiation transmitted through the imaging part is the same as the dose at the reference body thickness t_c, on the basis of the imaging part indicated by the imaging part information, the body thickness t indicated by the body thickness information, and the condition indicated by the condition information.

As described above, the derivation unit 66 of the console 10 according to this embodiment derives the set values of the tube voltage and the mAs value of the radiation emitting device 12 for emitting the radiation R such that the dose of the radiation transmitted through the imaging part is the same as the dose at the reference body thickness t_c, on the basis of the imaging part indicated by the imaging part information, the body thickness t indicated by the body thickness information, and the condition indicated by the condition information.

Therefore, according to the console 10 of this embodiment, it is possible to easily set appropriate tube voltage kV and mAs value corresponding to the imaging part and the body thickness t of the subject W for each imaging condition set in the radiation emitting device 12. In addition, according to the console 10 of this embodiment, appropriate tube voltage kV and mAs value corresponding to the imaging part and the body thickness t of the subject W are automatically set. Therefore, it is possible to reduce the burden on the user for setting.

Figure 9:
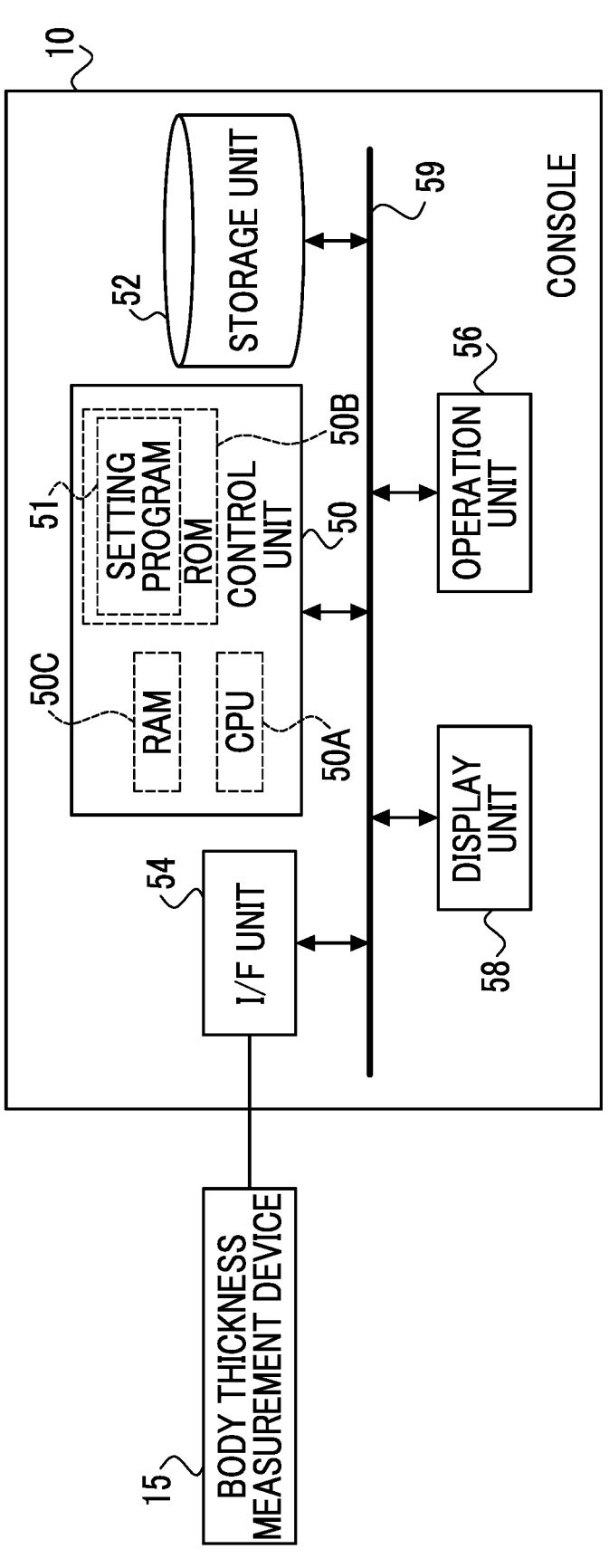
FIG. 9 is a functional block diagram illustrating an example of a functional configuration of the console according to the embodiment.

In addition, in this embodiment, a method using the distance image captured by the TOF camera 14 has been described as the method by which the console 10 acquires the body thickness of the subject W. However, the present disclosure is not limited to this method. For example, as illustrated in FIG. 9, the body thickness may be acquired by a body thickness measurement device 15 instead of the TOF camera 14.

For example, the body thickness measurement device 15 may be an imaging device that captures the distance image other than the TOF camera. For example, the following aspect may be used: a structured light method using an imaging device, which irradiates an object to be imaged with infrared light having a pattern and captures a distance image corresponding to reflected light from the object to be imaged, as the imaging device capturing the distance image is applied to capture the distance image. Further, for example, a depth-from-defocus (DFD) method that restores the distance on the basis of the degree of blurring of an edge region in the distance image may be applied. In the case of this aspect, for example, an aspect is known which uses a distance image captured by a monocular camera using a color aperture filter.

In addition, for example, a measurement device that measures a distance to an object to be measured, using ultrasonic waves, laser light, or the like emitted to the object to be measured, is given as an example of the body thickness measurement device 15. In this case, the second acquisition unit 62 acquires the measurement results of the STD and the SSD from the body thickness measurement device 15 and derives the body thickness t using the above-described Expression (1). Alternatively, the second acquisition unit 62 derives the body thickness t using the above-described Expression (2) on the basis of the SID, the TID, and the measurement result of the SSD acquired from the body thickness measurement device 15.

Further, for example, the body thickness measurement device 15 may be a caliper, a ruler, or the like. In this case, for example, an aspect may be used in which the user measures the body thickness of the subject W and inputs the measurement result using the operation unit 56 of the console 10. Furthermore, in this aspect, in a case in which the caliper, the ruler, or the like has a transmission function of transmitting the measurement result wirelessly or in a wired manner, the measurement result measured by the user may be transmitted from the body thickness measurement device 15 to the console 10 by the transmission function.

Moreover, for example, the body thickness measurement device 15 may be a visible light camera. The visible light camera is a so-called general camera and is a camera that captures a visible light image. Specifically, the visible light camera is a camera that receives visible light reflected by an object to be imaged using an imaging element and captures a visible light image on the basis of the received visible light. In this case, the visible light camera, which is the body thickness measurement device 15, captures, for example, a visible light image of the subject W and the imaging table 32 from the side surface (the x direction in FIG. 4) of the subject W and the imaging table 32. The second acquisition unit 62 may analyze the visible light image acquired from the body thickness measurement device 15 to derive the body thickness of the subject W.

In addition, in each of the above-described embodiments, the aspect in which the console 10, the radiation emitting device 12, and the radiography apparatus 16 are stationary in the radiography system 1 has been described. However, the radiography system 1 is not limited to this aspect. For example, a mobile cart, that is, a nursing cart may be used as the radiography system 1.

Further, in each of the above-described embodiments, the aspect in which the console 10 is an example of the setting device according to the present disclosure has been described. However, devices other than the console 10 may have the functions of the setting device according to the present disclosure. In other words, for example, the radiation emitting device 12, the radiography apparatus 16, or an external device other than the console 10 may have some or all of the functions of the first acquisition unit 60, the second acquisition unit 62, the third acquisition unit 64, and the derivation unit 66.

In addition, in each of the above-described embodiments, for example, the following various processors can be used as the hardware structure of processing units performing various processes such as the first acquisition unit 60, the second acquisition unit 62, the third acquisition unit 64, and the derivation unit 66. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in each of the above-described embodiments, the aspect in which the setting program 51 is stored (installed) in the storage unit 52 in advance has been described. However, the present disclosure is not limited thereto. The setting program 51 may be recorded on a recording medium, such as a compact disc read only memory (CD-ROM), a digital versatile disc read only memory (DVD-ROM), or a universal serial bus (USB) memory, and then provided. In addition, the setting program 51 may be downloaded from an external device through the network.

The disclosure of JP2020-161414 filed on Sep. 25, 2020 is incorporated herein by reference in its entirety.

All of the documents, the patent applications, and the technical standards described in the specification are incorporated by reference herein to the same extent as it is specifically and individually stated that individual documents, patent applications, and technical standards are incorporated by reference.

What is claimed is:

1. A setting device comprising at least one processor, wherein the processor is configured to:

acquire imaging part information indicating an imaging part of a subject whose radiographic image is captured by radiation emitted from a radiation emitting device;

acquire body thickness information indicating a body thickness of the subject in a direction in which the radiation is transmitted;

acquire condition information indicating that an imaging condition set in the radiation emitting device is one of a first condition in which a tube voltage value is a fixed value and a mAs value is a variable value, a second condition in which the tube voltage value is a variable value and the mAs value is a fixed value, or a third condition in which the tube voltage value is a variable value and the mAs value is a variable value;

derive a set value of the tube voltage and a set value of the mAs value of the radiation emitting device, for emitting the radiation such that a dose of the radiation transmitted through the imaging part is the same as a dose at a reference body thickness, based on a set of parameters including the imaging part indicated by the imaging part information and the body thickness indicated by the body thickness information, under each of the first condition, the second condition and the third condition; and for a particular derivation of the set value of the tube voltage and the set value of the mAs value, set one of the first condition, the second condition or the third condition, as a set condition, and then derive the set value of the tube voltage and the set value of the mAs value under the set condition.

2. The setting device according to claim 1, wherein the processor is configured to derive the set value of the tube voltage and the set value of the mAs value, using at least one of a source-to-image receptor distance (SID), the imaging part, a filter added to a radiation source, a type of a radiation detector that detects the radiation, adjustment information related to adjustment of the tube voltage with respect to the body thickness, or a concentration in automatic exposure control (AEC).

3. The setting device according to claim 1, wherein, in a case in which the condition indicated by the condition information is the first condition or the third condition, the processor is configured to derive the set value of the mAs value corresponding to the body thickness indicated by the body thickness information, using a linear attenuation coefficient for the tube voltage.

4. The setting device according to claim 1, wherein, in a case in which the condition indicated by the condition information is the second condition, the processor is configured to derive the set value of the tube voltage based on at least one of the imaging part indicated by the imaging part information, a reference tube voltage corresponding to the reference body thickness, or a filter added to a radiation source and the body thickness indicated by the body thickness information.

5. The setting device according to claim 1, wherein the processor is configured to acquire the imaging part information from an imaging menu.

6. The setting device according to claim 1, wherein the processor is configured to acquire the body thickness information by subtracting a source-to-skin distance (SSD) from a source target distance STD to derive the body thickness.

7. The setting device according to claim 1, wherein the processor is configured to acquire the body thickness information by subtracting a source-to-skin distance (SSD) and a target-to-image receptor distance (TID) from a source-to-image receptor distance (SID) to derive the body thickness.

8. The setting device according to claim 1, wherein the processor is configured to output the set value of the tube voltage and the set value of the mAs value to the radiation emitting device.

9. The setting device according to claim 2, wherein:

the reference body thickness is determined based on at least one of the imaging part, a race, a gender, an age, or a ratio of muscle to fat in the subject, and the processor is configured to use a reference tube voltage corresponding to the reference body thickness as the adjustment information.

10. A setting method executed by a processor, the setting method comprising:

acquiring imaging part information indicating an imaging part of a subject whose radiographic image is captured by radiation emitted from a radiation emitting device;

acquiring body thickness information indicating a body thickness of the subject in a direction in which the radiation is transmitted;

acquiring condition information indicating that an imaging condition set in the radiation emitting device is one of a first condition in which a tube voltage value is a fixed value and a mAs value is a variable value, a second condition in which the tube voltage value is a variable value and the mAs value is a fixed value or a third condition in which the tube voltage value is a variable value and the mAs value is a variable value; and deriving a set value of the tube voltage and a set value of the mAs value of the radiation emitting device for emitting the radiation such that a dose of the radiation transmitted through the imaging part is the same as a dose at a reference body thickness, based on a set of parameters including the imaging part indicated by the imaging part information and the body thickness indicated by the body thickness information, under each of the first condition, the second condition and the third condition; and for a particular derivation of the set value of the tube voltage and the set value of the mAs value, setting one of the first condition, the second condition or the third condition, as a set condition, and then deriving the set value of the tube voltage and the set value of the mAs value under the set condition.

11. A non-transitory computer-readable storage medium storing a setting program that causes a processor to execute a process comprising:

acquiring imaging part information indicating an imaging part of a subject whose radiographic image is captured by radiation emitted from a radiation emitting device;

acquiring body thickness information indicating a body thickness of the subject in a direction in which the radiation is transmitted;

acquiring condition information indicating that an imaging condition set in the radiation emitting device is one of a first condition in which a tube voltage value is a fixed value and a mAs value is a variable value, a second condition in which the tube voltage value is a variable value and the mAs value is a fixed value or a third condition in which the tube voltage value is a variable value and the mAs value is a variable value; and deriving a set value of the tube voltage and a set value of the mAs value of the radiation emitting device for emitting the radiation such that a dose of the radiation transmitted through the imaging part is the same as a dose at a reference body thickness, based on a set of parameters including the imaging part indicated by the imaging part information and the body thickness indicated by the body thickness information, under each of the first condition, the second condition and the third condition; and for a particular derivation of the set value of the tube voltage and the set value of the mAs value, setting one of the first condition, the second condition or the third condition, as a set condition, and then deriving the set value of the tube voltage and the set value of the mAs value under the set condition.

* * * * *